(12) United States Patent
Ronaghi et al.

(10) Patent No.: US 8,592,225 B2
(45) Date of Patent: Nov. 26, 2013

(54) ARRAY-BASED BIOACTIVATED NANOPORE DEVICES

(75) Inventors: Mostafa Ronaghi, Los Altos Hills, CA (US); Amir Ali Haj Hossein Talasaz, Los Altos, CA (US); Ronald W. Davis, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 1409 days.

(21) Appl. No.: 11/904,345

(22) Filed: Sep. 27, 2007

(65) Prior Publication Data
US 2012/0142016 A1    Jun. 7, 2012

Related U.S. Application Data

(60) Provisional application No. 60/847,860, filed on Sep. 28, 2006.

(51) Int. Cl.
*G01N 33/553*    (2006.01)

(52) U.S. Cl.
USPC ........ 436/525; 436/518; 436/524; 435/283.1; 435/287.2; 977/700; 977/701; 977/702; 977/778; 977/780

(58) Field of Classification Search
USPC ............ 436/518, 524, 525; 435/283.1, 287.2; 977/700, 701, 702, 778, 780
See application file for complete search history.

(56) References Cited

U.S. PATENT DOCUMENTS

| 6,676,904 | B1 | 1/2004 | Lee et al. | |
| 7,250,115 | B2* | 7/2007 | Barth | 216/56 |
| 2003/0170687 | A1* | 9/2003 | Chilkoti et al. | 435/6 |
| 2005/0023156 | A1 | 2/2005 | Ramsey | |
| 2005/0074778 | A1* | 4/2005 | Letant et al. | 435/6 |
| 2005/0202446 | A1 | 9/2005 | Yang et al. | |

OTHER PUBLICATIONS

Amir Ali H. Talasaz, et al., "Fabrication of customized bioactivated nanopore devices," Proc. Micro Total Analysis Systems, 2005,
Amir Ali H. Talasaz, "Bioactivated Nanopores for molecular analysis," PhD thesis submitted to Stanford University Department of Electrical Engineering, Sep. 2007.
Peng Chen, et al., "Atomic layer deposition to fine-tune the surface properties and diameters of fabricated nanopores," Nano Letters, 2004, vol. 4, 1333-1337.
David W. Deamer, et al., "Nanopores and nucleic acids: prospects for ultrarapid sequencing," Tibtech, Apr. 2000, vol. 18, 147-151.

(Continued)

*Primary Examiner* — Melanie Y Brown
(74) *Attorney, Agent, or Firm* — David J. Aston; Peters Verny, LLP

(57) ABSTRACT

A nanopore device capable of single molecule detection is described. The nanopores are formed in thin, rigid membranes and modified by a sputtered metal that forms an overhang during application. The overhang causes the pore to be narrower in a certain region, allowing passage of only a single molecule through the pore at a time, or binding to a biomolecule on the pore to be detected by a change in ionic current flow through the nanopore. Embodiments include a silicon nitride membrane formed on a silicon substrate and having a nanopore drilled with a focused ion beam system, followed by gold sputtering onto the membrane. Devices are formed with one or more nanopores and chambers having electrodes on either side of the nanopore.

22 Claims, 14 Drawing Sheets

(56) References Cited

OTHER PUBLICATIONS

Advanced Materials, Supporting Information for Advanced Materials, adma.200501500, Wiley-VCH 2006, 69451 Weinheim, Germany.

Daniel Fologea, et al., "Detecting single stranded DNA with a solid state nanopore," Nano Letters, 2005, vol. 5, 1905-1909.

A. J. Storm, et al., "Translocation of double-stranded DNA through a silicon oxide nanopore,"Physical Review E, 2005, vol. 71,051903 1-10.

Jiali Li, et al., "Ion-beam sculpting at nanometre length scales," Nature, Jul. 2001, vol. 412, 166-169.

Mark C. Barnes, et al., "The mechanism of old deposition by thermal evaporation," J. Ceramic Processing Research, 2000, vol. 1, 45-52.

Michelle A. Brusatori, et al., "Protein adsorption kinetics under an applied electric field: An optical waveguide lightmode spectroscopy study," PhD thesis submitted to Wayne State University Department of Chemical Engineering, 2001.

J. B. Heng, et al., "The electromechanics of DNA in a synthetic nanopore," Biophys. J. BioFAST, Nov. 2005, doi: 10.1529/biophysj. 105.070672.

P. Ramirez, et al., "Synthetic nanopores with fixed charges: An electrodiffusion model for ionic transport," Physical Review E, 2003, 011910 1-8.

Amirali H. Talasaz, et al., "Prediction of protein orientation upon immobilization on biological and nonbiological surfaces" PNAS, Oct. 2006, vol. 103, 14773-14778.

M. H. Sohn, et al., "A novel large area ion plating process," 46th Annual Techincal Conference Proceedings, 2003, Society of Vacuum Coaters, ISSN 0737-5921.

Amirali H. Talasaz, et al., "Modeling of the bioactivated nanopore devices," Proceedings of the 28th IEEE EMBS Annual International Conference, New York city, USA, Aug. 30-Sep. 3, 2006, ThEP7.5.

Amirali H. Talasaz, et al., "Cell trapping in activated micropores for functional analysis," Proceedings of the 28th IEEE EMBS Annual International Conference, New York city, USA, Aug. 30-Sep. 3, 2006, ThEP7.5.

\* cited by examiner

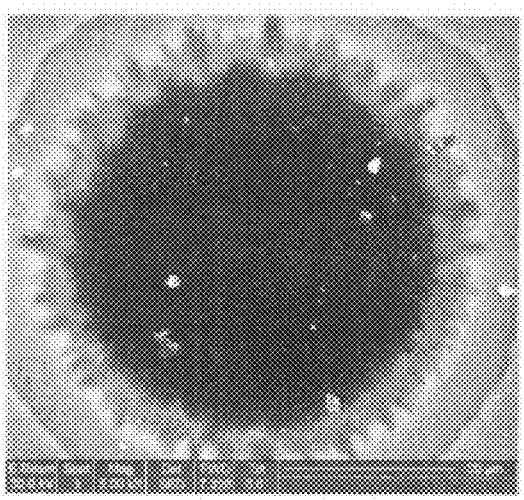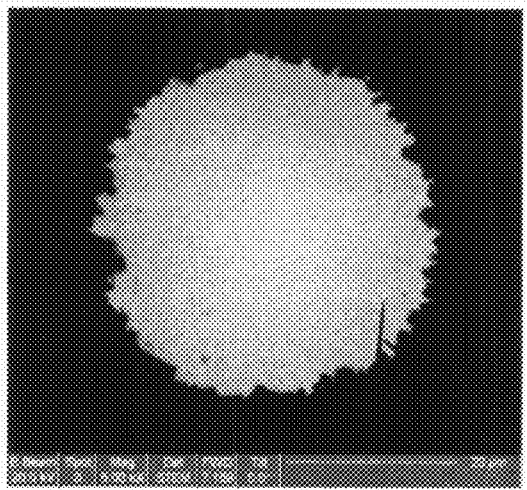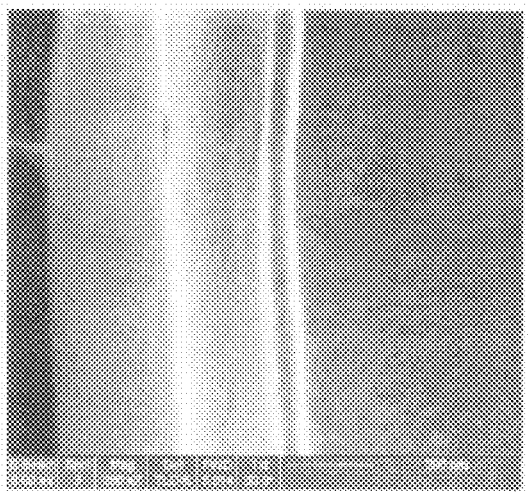
Fig. 2 A-C

Covalent Enzyme Immobilization

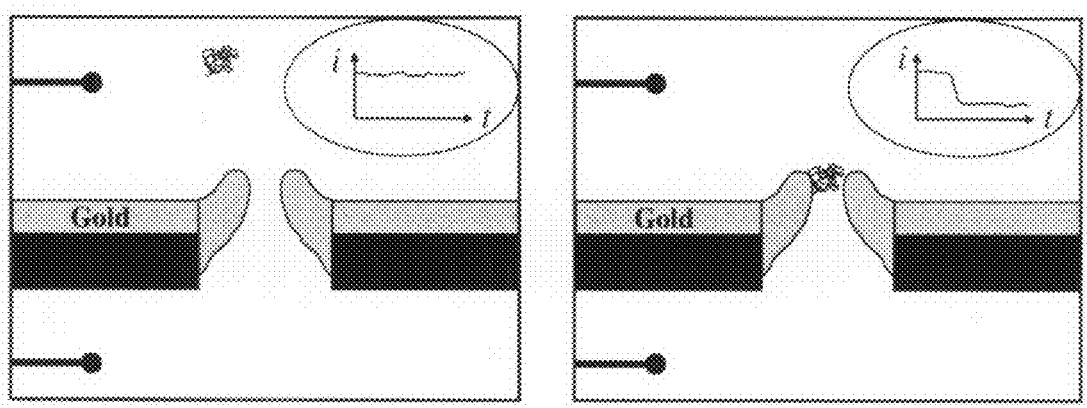
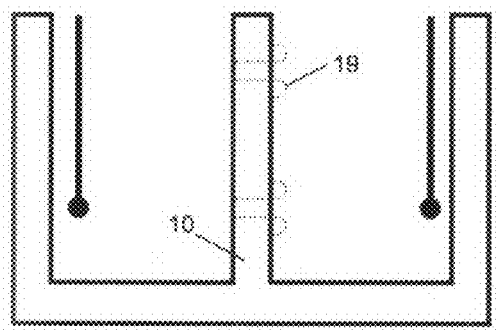
Fig. 7 A-B

Attachment of Proteins in Nanopores

Fig. 14 A-C

SEQUENCE LISTING

```
<160> NUMBER OF SEQ ID NOS: 4

<210> SEQ ID NO 1
<211> LENGTH: 21
<212> TYPE: DNA
<213> ORGANISM: Artificial
<220> FEATURE:
<223> OTHER INFORMATION: DNA Probe

<400> SEQUENCE: 1
ggatcatgta actcgccttg a                                           21

<210> SEQ ID NO 2
<211> LENGTH: 19
<212> TYPE: DNA
<213> ORGANISM: Artificial
<220> FEATURE:
<223> OTHER INFORMATION: DNA probe
```

```
-continued

<400> SEQUENCE: 2
gggagggctt accatctgg                                                      19

<210> SEQ ID NO 3
<211> LENGTH: 22
<212> TYPE: DNA
<213> ORGANISM: Artificial
<220> FEATURE:
<223> OTHER INFORMATION: DNA Probe

<400> SEQUENCE: 3
gggatcatgt aactcgcctt ga                                                  22

<210> SEQ ID NO 4
<211> LENGTH: 135
<212> TYPE: DNA
<213> ORGANISM: Artificial
<220> FEATURE:
<223> OTHER INFORMATION: DNA Probe

<400> SEQUENCE: 4
gagtaagtag ttcgccagtt aatagtttgc gcaacgttgt tgccattgct acaggcatcg         60
tggtgtcacg ctcgtcgttt ggtatggctt cattcagctc cggttcccaa cgatcaaggc        120
gagttacatg atccc                                                         135
```

ARRAY-BASED BIOACTIVATED NANOPORE DEVICES

CROSS-REFERENCE TO RELATED APPLICATIONS

This application claims priority from U.S. Provisional Patent Application No. 60/847,860 filed on Sep. 28, 2006, which is hereby incorporated by reference in its entirety.

STATEMENT OF GOVERNMENTAL SUPPORT

This invention was made with Government support under contract PO1 HG000205 awarded by the National Institutes of Health. The Government has certain rights in this invention.

REFERENCE TO SEQUENCE LISTING

Applicants assert that the paper copy of the Sequence Listing is identical to the Sequence Listing in computer readable form found on the accompanying computer disk. Applicants incorporate the contents of the sequence listing by reference in its entirety.

BACKGROUND OF THE INVENTION

1. Field of the Invention

The present invention relates to the field of biosensors for detecting molecular interactions and, further, to devices having nanopores to which are attached active biological molecules.

2. Related Art

As described in US PGPUB 2005/0186629, manipulating matter at the nanometer scale is important for many electronic, chemical and biological advances (See Li et al., "Ion beam sculpting at nanometer length scales," *Nature,* 2001, 412: 166-169). Such techniques as "ion beam sculpting" have shown promise in fabricating molecule scale holes and nanopores in thin insulating membranes. These pores have also been effective in localizing molecular-scale electrical junctions and switches.

Artificial nanopores have been fabricated by a variety of research groups with a number of materials. Generally, the approach is to fabricate these nanopores in a solid-state material or a thin freestanding diaphragm of material supported on a frame of thick silicon to form a nanopore chip. Some materials that have been used to date for the diaphragm material include silicon nitride and silicon dioxide.

The flow of materials through nanopores can also be externally regulated. What is believed to be the first artificial voltage-gated molecular nanosieve was fabricated (Matsuhiko Nishizawa, Vinod P. Menon, Charles R. Martin, "Metal nanotubule membranes with electrochemically switchable ion-transport selectivity," *Science,* 5 May 1995, 268:700-702) at Colorado State University in 1995. This membrane contained an array of cylindrical gold nanotubules with inside diameters as small as 1.6 nanometers. When the tubules are positively charged, positive ions are excluded and only negative ions are transported through the membrane. When the membrane receives a negative voltage, only positive ions can pass. Similar nanodevices may combine voltage gating with pore size, shape, and charge constraints to achieve precise control of ion transport with significant molecular specificity. A sensitive ion channel switch biosensor was built by an Australian research group (B. Cornell, V. Braach-Maksvytis, L. King, P. Osman, B. Raguse, L. Wieczorek, R. Pace, "A biosensor that uses ion-channel switches," *Nature,* 5 Jun. 1997, 387:580-583.) The scientists estimated that their sensor could detect a minute change in chemical concentration equivalent to one part in roughly 1018.

Experiments have been conducted using an electric field to drive a variety of RNA and DNA polymers through the central nanopore of an alpha-hemolysin protein channel mounted in a lipid bilayer similar to the outer membrane of a living cell (A. Meller, L. Nivon, E. Brandin, J. Golovchenko, D. Branton, "Rapid nanopore discrimination between single polynucleotide molecules," *Proc. Natl. Acad. Sci.* (USA), 1 Feb. 2000, 97:1079-1084). Researchers have reported that the individual nucleotides comprising the polynucleotide strands must be passing single-file through the 2.6 nanometer-wide nanopore, and that changes in ionic current could be used to measure polymer length, and that the nanopore could be used to rapidly discriminate between pyrimidine and purine segments (the two types of nucleotide bases) along a single RNA molecule. Nanopore devices which can discriminate between purine and pyrimidine molecules have been reported (D. W. Deamer, M. Akeson, "Nanopores and nucleic acids: prospects for ultrarapid sequencing," *Trends Biotechnol,* April 2000, 18:147-15). Differences in ionic blockage current were measured. Because nanopores can rapidly discriminate and characterize DNA polymers at low copy number, future refinements of this experimental approach may eventually provide a low-cost high-throughput method for very rapid genome sequencing.

Although nanopore-based sensors have been explored for single nucleic acid molecule sequencing, they still cannot claim success. But they offer one of the most promising approaches for structural analysis of single molecules of few nanometers diameter.

PATENTS AND PUBLICATIONS

US 2005/0074778, entitled "Functionalized apertures for the detection of chemical and biological materials, by to Letant (published Apr. 7, 2005) discloses nanometer to micron scale functionalized apertures constructed on a substrate made of glass, carbon, semiconductors, or polymeric materials, and arrays of such apertures. In one embodiment, a macrocyclic ring is cross-linked at the opening of an aperture and the ring is attached to a single probe.

U.S. Pat. No. 5,795,782, entitled "Characterization of individual polymer molecules based on monomer-interface interactions" to Church (issued Aug. 18, 1998) discloses a method for evaluating a polymer molecule (such as DNA). Two separate pools of liquid medium and an interface between the pools are provided. A voltage difference is applied across the pools for determination of the concentration and/or sequence of polymer. The interface includes ion permeable passages (pores), which can be proteins or mechanical perforations of a membranous material.

US 2005/0023156, entitled "Nanostructured material transport devices and their fabrication by application of molecular coatings to nanoscale channels" published Feb. 3, 2005 by Ramsey describes various substrates having nanopores and attached to probes such as proteins, antibodies, nucleic acids and chelators. Chemical sensing information is derivable from the temporal and/or magnitude of the current variations measured through the voltage biased orifice.

US 2006/0030151 to Peijun et al., published Feb. 9, 2006, entitled "Sputter deposition and etching of metallization seed layer for overhang and sidewall improvement," describes aspects of sputtering, including overhangs. Overhangs are believed to arise principally from the neutral component of the sputter flux, which is somewhat isotropic with approximately a cosine distribution about the vertical axis. Such overhangs may introduce serious problems in semiconductors. The overhangs progressively grow and narrow the throat of a hole during the sputter deposition, thus effectively increasing the aspect ratio and thus further decreasing the sputter flux into the hole.

US 2005/0186629 to Barth, published Aug. 25, 2005, entitled "Nanopore device and methods of fabricating and using the same," (referenced above) discloses devices including first and second fluid containment members separated by a fluid barrier having a single nanopore therein. The nanopore provided fluid communication between the first and second fluid containment members.

King et al., "Probing Nanotube-Nanopore Interactions," *Physical Review Lett.*, Nov. 18, 2005, 95, 216103, disclose a nanoscale system consisting of a nanotube threaded through a nanopore in aqueous solution. A single nanopore was made in a freestanding membrane of silicon nitride. The membrane separated two reservoirs of conducting electrolyte solution [1 M KCl, 10 mM TRIS-HCl, 1 mM EDTA, pH 8]. Electrical contact to the solution was achieved though Ag/AgCl electrodes. A carbon nanotube to be threaded through the nanopore was affixed to the tip of an AFM cantilever.

Chen et al., "Atomic Layer Deposition to Fine-Tune the Surface Properties and Diameters of Fabricated Nanopores," *NanoLetters*, 2004, 4(7):1333-1337, disclose that atomic layer deposition of alumina enhanced the molecule sensing characteristics of fabricated nanopores by fine-tuning their surface properties, reducing 1/f noise, neutralizing surface charge to favor capture of DNA and other negative polyelectrolytes, and controlling the diameter and aspect ratio of the pores with near single Ångstrom precision. Nanopores were fabricated as described by Li et al., in *Nature* 2001:412, 166. The authors used ~200 nm thick $Si_3N_4$ membranes.

Fologea et al, "Detecting single stranded DNA with a solid state nanopore," *NanoLetters*, 2005, 5(10) 1905-1909, describe the use of voltage-biased solid-state nanopores used to detect individual single stranded DNA molecules. A highly alkaline environment was found to be required to obtain freely translated DNA molecules. Using a 4 nm silicon nitride nanopore, an experimental set up was prepared using ionic solution reservoirs with a chip having a nanopore in between.

Hou et al., "Template-synthesized protein nanotubes," *Nano Lett.* 2005 February, 5(2):231-4 disclose a method for preparing protein nanotubes within the pores of a nanopore alumina template membrane. The method entails alternately exposing the template membrane to a solution of the desired protein and then to a solution of glutaraldehyde, which acts as cross-linking agent to hold the protein layers together. After the desired number of layers has been deposited on the pore walls, the alumina template can be dissolved to liberate the protein nanotubes. Glucose oxidase nanotubes prepared in this way were shown to catalyze glucose oxidation.

BRIEF SUMMARY OF THE INVENTION

The following brief summary is not intended to include all features and aspects of the present invention, nor does it imply that the invention must include all features and aspects discussed in this summary.

The present invention comprises, in certain aspects, combinations of the following features:
1. A rigid membrane support;
2. At least one aperture (nanopore) through the support;
3. An annular overhang produced at one end of the aperture, e.g. by sputtering a metal such as gold onto the surface of the support, the overhang forming the walls of a nanopore, which has a reduced diameter relative to the original aperture;
4. A single probe molecule (or multiple molecules) attached over or within the overhang.
5. Means for monitoring ionic current through the aperture for detecting interaction between the probe and analyte; and
6. An array of such apertures in a single membrane, i.e., a predetermined number of apertures.

The present invention also comprises, in certain aspects, the manufacture and use of an array device comprising a plurality of nanopores. The array may be contained on a single inert membrane and fabricated by depositing Cr/Au/Pd on the membrane after drilling holes in the membrane. The nanopore array is bathed in a fluid, and electrodes are arrayed on either side of the membrane. A method of measuring an analyte in a sample comprising contacting the analyte with a specific binding partner for the ligand, wherein the binding partner is immobilized on a biosensor having a plurality of nanopore structures, each comprising a nanopore aperture in a membrane, the nanopore comprising an annular overhang for reducing nanopore size to less than about 100 nm, and further comprising electrodes and a current sensing device for measuring a change in current through the nanopores upon binding of the analyte in the sample to the binding partner.

BRIEF DESCRIPTION OF THE DRAWINGS

FIG. 2 is a series of SEM micrographs showing: (A) secondary electron in SEM; (B) scanning tunneling electron image; and (C) membrane thickness measurement (~50 nm after 15 nm gold deposition to reduce charging);

FIG. 7 is a diagrammatic representation of attachment of a biological molecule to gold in a nanopore (A), and a device for utilizing the functionalized nanopore (B);

DETAILED DESCRIPTION OF THE PREFERRED EMBODIMENT

Definitions

Figure 1:
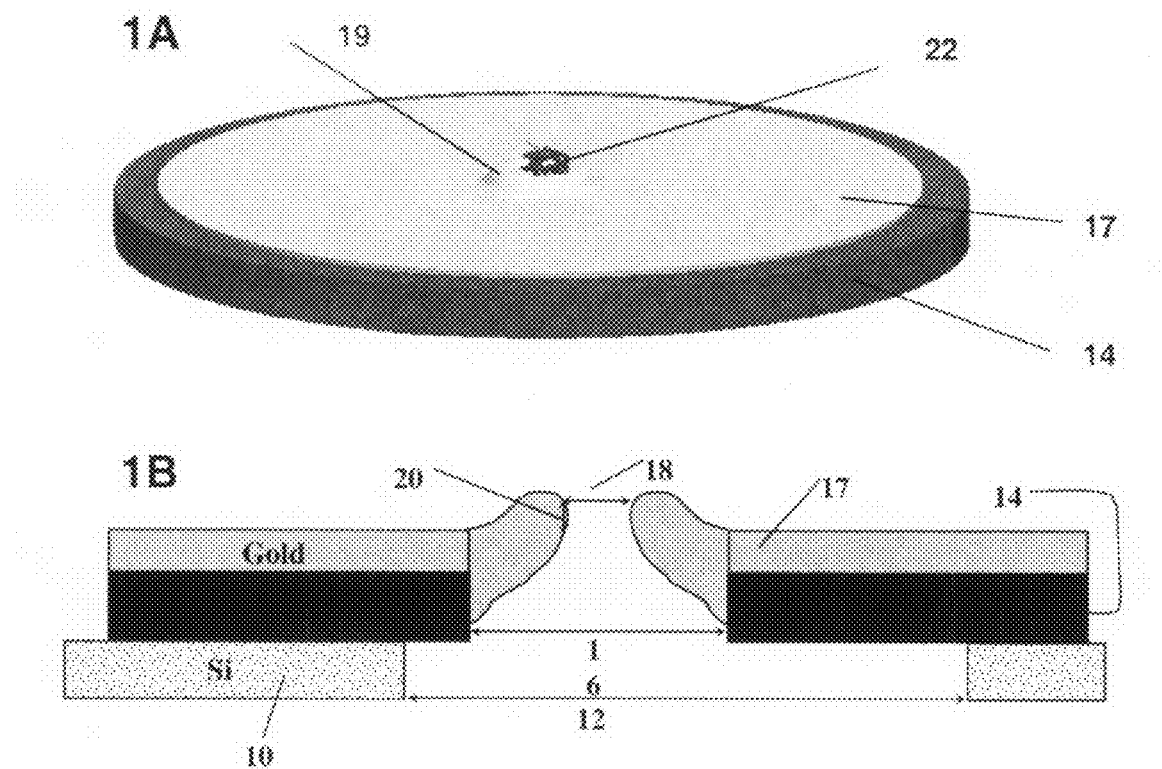
FIG. 1 is a diagram showing, in 1A, a view of a typical bioactivated nanopore in which a biological macromolecule is attached in the nanopore; and in 1B, a cross section schematic of a customized nanopore, prior to attachment of a biological molecule to the gold.
Figure 3:
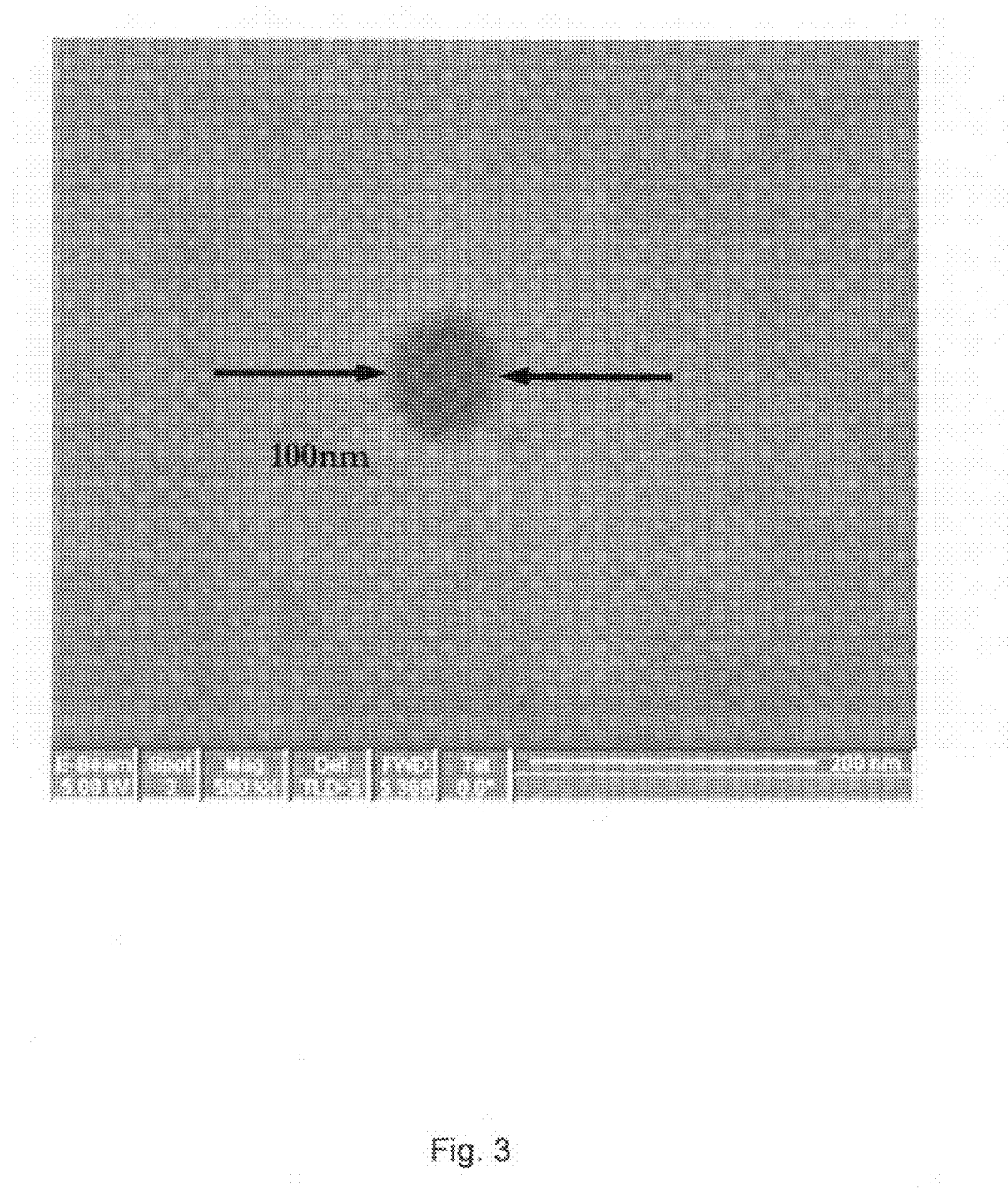
FIG. 3 is an SEM image showing an as-drilled nanopore in a silicon nitride membrane.
Figure 4:
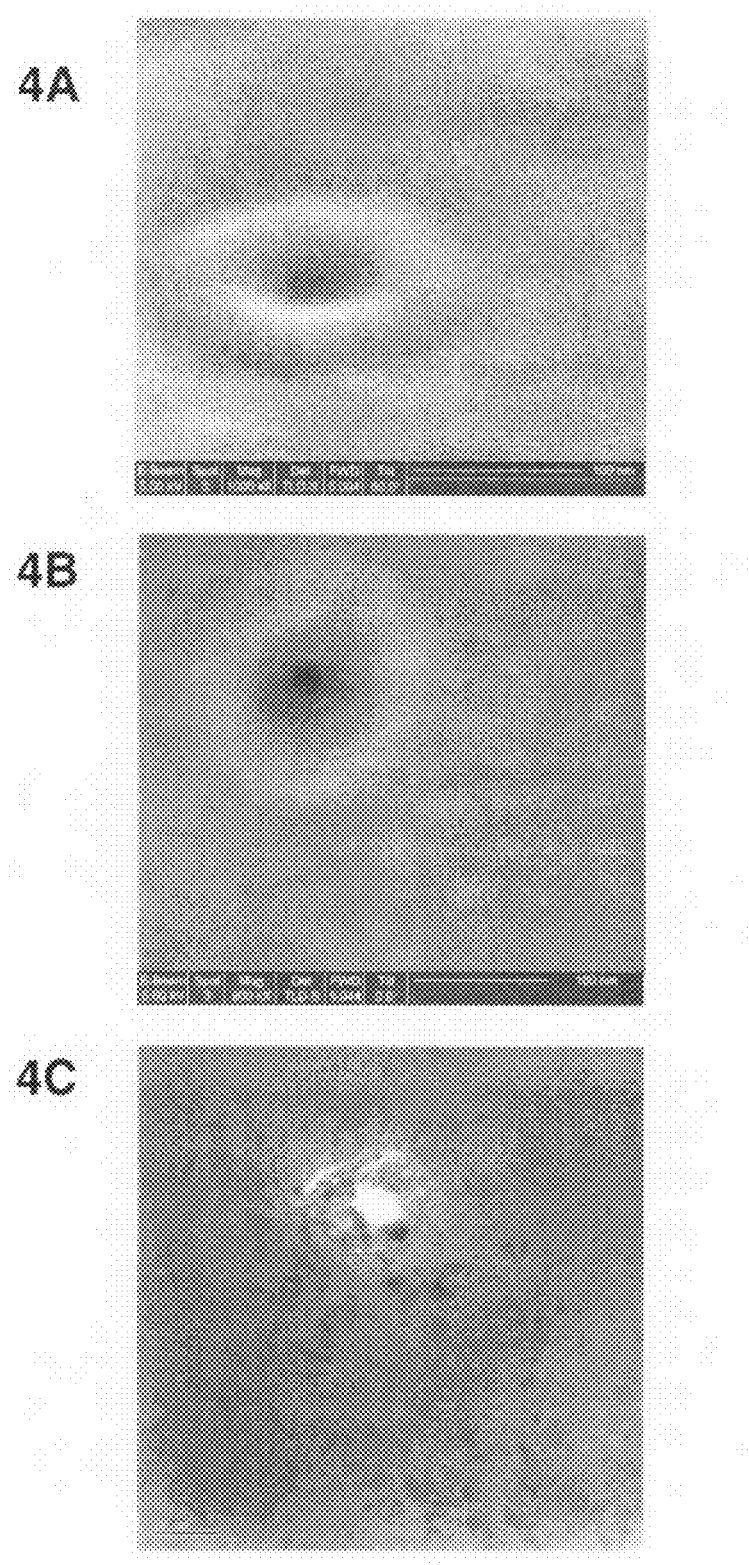
FIG. 4 is a series of SEM images, (A) 20 nm hole in the silicon nitride membrane (60° tilted sample), (B) SEM image of 20 nm hole in the silicon nitride membrane (top view) (C) TEM image of the 20 nm nanopore.

All terms are used in their conventional sense as understood by workers in the field. The following definitions are intended to provide further clarity to those terms.

The term "alkyl thiol" means an alkyl group terminated at one end by a thiol (—SH) group. The alkyl is preferably three to twenty carbons long, and may be optionally substituted with various surface-modifying groups. As described below, the alkyl thiols used herein have reactive groups on an end of the molecule distal to the thiol end. The preferred alkyl thiol used in the present work is —COOH or —OH terminated, such group also preferably at an end opposite to the end with an —SH group.

The term "biosensor" means an analytical device composed of a chemical or biological element (probe) in intimate contact with a physical transducer, which together relate the concentration of a target analyte to a measurable signal when the biological or chemical element binds specifically with an analyte.

The term "biopolymer" means is a polymer of one or more types of repeating units, regardless of the source (e.g., biological (e.g., naturally-occurring, obtained from a cell-based recombinant expression system, and the like) or synthetic). Biopolymers may be found in biological systems and particularly include polypeptides, polynucleotides, proteoglycans, lipids, sphingoedgeids, etc., including compounds containing amino acids, nucleotides, or a mixture thereof. Preferred biopolymers include polypeptides, including enzymes and antibodies, and polynucleotides.

The term "membrane" refers to any relatively thin material, which can be perforated to from a nanopore. Typical membrane materials include rigid materials such as silicon nitride and silicon oxide, but may alternatively be formed from such materials as metal or other silicon compounds, as exemplified below. The term is understood in connection with a nanopore formed in the membrane. The membrane is impermeable to the analyte except for the nanopore or pores to be formed in it.

The term "nanopore" means a hole completely through a substrate or membrane, generally, but not necessarily, cylindrical in shape, between about 20 nm to 1 μm in diameter, preferably about 100 nm, prior to further processing (i.e., narrowing). The present nanopores will preferably be narrowed from the as-drilled size by addition of a secondary layer, narrowing the nanopore to about, e.g., 20 nm, with an effective channel length (i.e., length at the selected diameter) of about 5-20 nm.

The term "protein" means a molecule having at least two covalently attached amino acids, which includes proteins, polypeptides, oligopeptides and peptides. A polypeptide may be made up of naturally occurring amino acids and peptide bonds, synthetic peptidomimetic structures, or a mixture thereof. Thus "amino acid", or "peptide residue", as used herein encompasses both naturally occurring and synthetic amino acids. For example, homo-phenylalanine, citrulline and norleucine are considered amino acids for the purposes of the invention. "Amino acid" also includes imino acid residues such as proline and hydroxyproline. The side chains may be in either the D- or the L-configuration. The present proteins are preferably used in their native, i.e., functional state, such as antibody binding to antigen, enzyme acting on substrate, receptor binding to ligand, etc.

The term "overhang" means a bulge formed when a thin film is deposited inside and around a fine hole formed in the surface of a substrate. There is a tendency for the thin film to build up and create a bulge around the edge of the opening of the hole. The thin film that makes up this bulge portion is called an "overhang." See, e.g., U.S. Pat. No. 6,077,403, "Sputtering device and sputtering method." Overhangs resulting from copper sputtering are illustrated in Sohn et al., "A Novel Large Area Ion Plating Process," 2003 Society of Vacuum Coaters 505:856-7188.

The term "about" is intended to have its normal meaning and, in connection with a numerical range, refers to all numbers within that range. It accounts for routine inaccuracy inherent in measurement and small (e.g., <10%) variations of an exact number.

Overview

Described below are bioactivated nanopores, formed in customized nanopore devices with a biological macromolecule attached in the pore as the probe. These devices are capable of detection and analysis of interactions between the attached biomolecule and the molecules in the analyte at a single molecule level.

Referring now to FIGS. 1A and 1B, an embodiment of the present invention is illustrated as fabricated in a silicon wafer support, e.g., 300 μm thick, having a first opening 12 over which is placed a membrane 14. The support may be any inert, rigid material, including metal and glass.

As is known in the art, a combination of semiconductor device fabrication techniques: photolithography, reactive ion etching, and wet chemical etching, etc. may be used to create a freestanding membrane supported by an inert (e.g., silicon) substrate. To make nanometer scale pores in the membrane, a focused ion beam machine or e-beam lithography may be used. One may also use means for controlling the lateral mass transport of matter across a surface on nanometer length scales, called ion beam sculpting may also be used. This technique is further described in Li, D. Stein, C. McMullan, D. Branton, M. J. Aziz, and J. Golovchenko, "Nanoscale Ion Beam Sculpting", *Nature,* 2001, 412, 166, and in US 2005/0006224 to Golovchenko, et al., published Jan. 13, 2005, entitled "Pulsed ion beam control of solid state features." Briefly, in this technique, the membrane is exposed to a periodic flux of ions having a characteristic ion exposure duty cycle. The periodic ion flux exposure is carried out at a first exposure temperature and then at a second exposure temperature that is greater than the first exposure temperature, to cause transport, within the membrane of material to the structural feature (nanopore) in response to the ion flux exposure to change at least one physical dimension by locally adding material of the structure to the feature. This technique is further described in USPGPUB 2005/0186629, referenced above.

The membrane 14 is thinner than the Si wafer, typically about 20-100 nm (e.g., 75 nm) thick. Opening 12 may be created by back etching down to the silicon nitride layer 14, as is known in the art, using e.g., KOH or reactive ion etching. The silicon nitride membrane 14 is then perforated with an opening 16, smaller than opening 12. This perforation may be done by electron beam patterning followed by reactive ion etching, focused electron beam or ion beam etching, and may be on the order of between 20 nm and 1 μm, preferably about 100 nm.

The membrane 14 most preferably comprises silicon nitride, more preferably silicon dioxide, but comprises one or more of one of a group including but not limited to a polymer, photoresist, SU8 photoresist, epoxy, polyimide, Parylene® (a silicone polymer), silicon oxynitride, silicon carbide, silicon-rich silicon nitride, TEOS oxide, plasma nitride, an insulator, a semiconductor, and a metal, provided that the membrane can be milled to provide a nanopore, coated with a metal, and has sufficient rigidity at the thinness desired.

Next, gold sputtering is used to decrease the annular overhang to an effective diameter of about 1 nm-100 nm, depending on the application. For the present work, an effective nanopore diameter of 20 nm is used. For other applications, such as nucleic acid analysis, a narrower aperture, e.g., 1-2 nm may be formed. The diameter of the nanopore as formed by the overhang is selected on the basis of the analyte molecule. Only one molecule in a sample will pass through the nanopore at a time.

The sputtering produces a continuous, essentially planar (except in the vicinity of the nanopore) gold surface 17, attached to the membrane, within the area sputtered, but the process produces "overheads" or "overhangs," inside and around the nanopores, which are used according to the present description. As shown in FIG. 1B, the overhang curves upward above the silicon nitride in a generally frusto-conical shape, as shown at 19 in FIG. 1A, and, on the inside, has a thickness which effectively reduces the pore diameter 18, as well as the effective channel length 20. That is, the pore diameter of significance has been reduced to about 20 nm. An effective channel length of 5-20 nm as bounded by the overhang exists in the axial direction 20. By measuring the ionic current passing through the nanopore it is possible to estimate this effective channel length to be typically between 5-10 nm. The pore diameter is adjustable (e.g., down to 2 nm) by controlling the thickness of the sputtered film. The thin silicon nitride membrane had applied to it a layer of chromium, then gold and/or palladium, to which a self-assembled monolayer, as described below, is attached.

The overhang allows the fabrication of a unique nanopore geometry having a small aspect ratio (length of channel divided by diameter). Preferably the aspect ratio (1/d) of the present devices is less than about 0.1 to 5. The advantage of a small aspect ratio is that the ionic current change, upon transportation of any molecule through the pore or interaction with the pore or probe molecule adjacent to the pore, will be greater as compared with a pore having a larger aspect ratio. The sensitivity of detection will be increased and measurements with better resolution are achievable. The diameter of the annular overhang can be selected, i.e., tuned, as required for a particular probe molecule.

As shown in FIG. 1A, conventional linker chemistry is used to attach a biological molecule (probe) 22 over or within the overhang.

Drilling Nanopores in Membrane

First, circular ultrathin low-stress silicon nitride membranes were fabricated. The thickness of the film is 30 nm and its diameter is 50 um. The fabricated membrane possesses adequate mechanical strength and is inert to aggressive chemicals. The membranes were fabricated by chemical vapor deposition. Alternatively, they may be purchased from SPI Supplies (West Chester, Pa.).

Next, reproducible 100 nm pores were milled in silicon nitride nanomembranes of 30 nm thick. A dual FIB (focused ion beam) system with a 30-KV gallium beam was used to drill the pores in the nanomembrane and a circular hole inside the membrane is formed. FIGS. 2A, 2B, 3 and 4 show representative pores. The three-dimensional geometry of the final nanopores should be close to the size of the probe molecule. Moreover, due to the requirement of chemical binding of the probe molecule to the nanopore, the surface of the nanopore(s) should offer adequate binding affinity. Gold is an excellent layer for this purpose, and its application is described below. FIG. 2C shows membrane thickness after gold deposition, which is 50 nm after gold deposition of 15 nm. Typically, the metal deposition should be between 5 and 70 nm thick, e.g., 15 nm thick, depending on ultimate pore size desired.

Other methods for forming nanopores may be used. For example, another suitable method for forming a nanopore is reported in Heng et al., "The Electromechanics of DNA in a Synthetic Nanopore," *Biophys J BioFAST*, published on Nov. 11, 2005 as doi:10.1529/biophysj.105.070672. A nanopore was created in a membrane by stimulated decomposition and sputtering using a tightly focused electron beam in a JEOL 2010F transmission electron microscope (TEM) operating at 200 keV. TEM images taken at a tilt angle of 0° showed circular pores with apparent diameter of $d0=1.0\pm0.2$ nm, $1.9\pm0.2$ nm and $3.0\pm0.2$ nm in a Si3N4 membrane nominally 10 nm thick. Scanning tunneling microscopes have also been used to create nanoscale pores.

Sputtering Gold Over Nanopores

Gold sputtering has been employed as an additional step to decrease the pre-known drilled pore size to the desired value. Gold overhangs formed during sputtering help form low-aspect ratio pores suitable for single-molecular bioactivated nanopore sensors.

The size of previously FIB-drilled nanopore in the membrane was thus further reduced to 20 nm by gold film sputtering. The present process flow for fabrication of the customized nanopores has been shown to make 20 nm gold-covered nanopores reproducibly.

The sputtering process was performed in a Metallica Sputtering system. (For details see http://snf.stanford.edu/Equipment/metalica/Equip.html.) First a thin layer of chromium, 5 nm, is sputtered on the membrane as an adhesion layer. Then a gold thin film is sputtered. The thickness of the gold film is controlled by controlling the sputtering time.

Other methods besides sputtering may be used for depositing a metal (gold) layer, which will also result in the desired overhangs, such as gold evaporation. See, e.g., Barnes et al., "The mechanism of gold deposition by thermal evaporation," *Journal of Ceramic Processing Research*, 2000, Vol. 1, No. 1, pp. 45-52. In this case, the substrate is tilted and rotated to produce the desired overhang configuration.

A wide variety of metals in addition to gold may be applied by sputtering, including titanium, tantalum, chromium, tungsten, hafnium, zirconium, niobium, aluminum, platinum, and palladium. Active proteins may be attached to these metals as described in US 2005/0250193 to Dziedzic, et al., published Nov. 10, 2005, entitled "Process for immobilization of protein catalysts, product, and use." In that method, an adhesive is applied to the surface of the support. It is preferred to use a one-component, solvent-based adhesive. The adhesive to be diluted in solvent so that it is easier to apply a thin layer to the support surface. After applying the adhesive, it is preferred to evaporate any solvent in the adhesive layer. A globular protein layer is then applied onto the adhesive layer.

Attachment of Biological Molecules

Silicon nitride is practically inert for biomolecule attachment, whereas further surface chemistry modifications can be performed on gold through forming self-assembled monolayers (SAMs) of alkyl thiols and the like. Nanopores can be bioactivated through covalent immobilization of biological macromolecules, like antibodies, proteins or DNA single strands in the pore through covalent binding to the SAM.

The present electrode metal surfaces, when covered by a thin surface oxide film, can also be functionalized by reagents such as chloro or alkyl silanes. By analogy with silica surfaces, Pt/PtO, Au/AuO and $SnO_2$ surfaces have many M-OH sites (where M is the metal) and when they are contacted with, for example, a solution of dichlorodimethylsilane [$Cl_2Si(CH_3)_2$] under anhydrous conditions the organosilane reagent becomes immobilized by formation of chemically stable -MOSi— bonds (where MO represents the surface metal oxide). To bond an enzyme to a silanized surface, it is important that the organosilane reagent itself bears chemical functionality such as a primary amine group or a carboxylic acid. A particularly useful reagent in this context is propyl amino silane [$(CH_3CH_2O)3Si(CH_2)3NH_2$] which will not only functionalize a metal electrode but will then allow coupling chemistry to take place with proteins through the attendant amine grouping.

Figure 5:
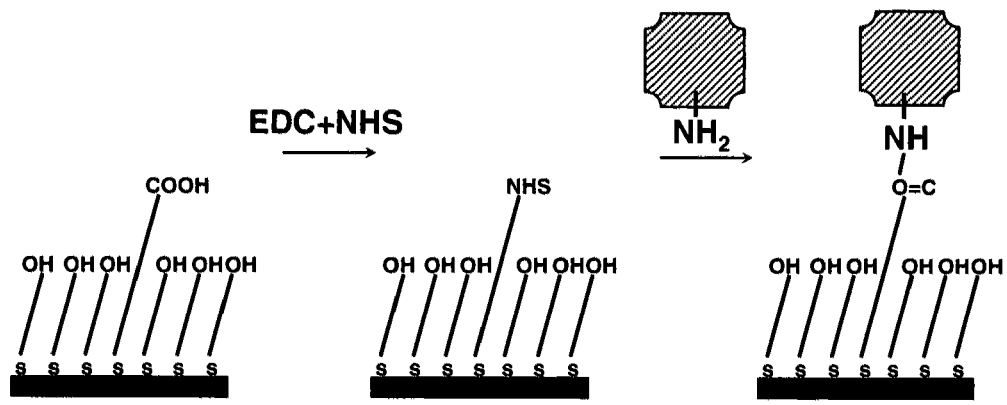
FIG. 5 is a schematic diagram showing covalent enzyme immobilization to gold.

As shown in FIG. 5, covalent enzyme immobilization may be accomplished by attaching an alkyl thiol to the gold surface. In addition to the —SH group at one end of the alkyl group, the alkyl thiol will further comprise a reactive group at another end of the molecule. As shown, such reactive groups include —OH, COOH, or mixtures thereof. The reactive group is selected according to the biomolecule to be linked to the surface. —COOH groups are preferred for coupling to N-terminal amines of proteins. As indicated, a protein having a pendant $NH_2$ will be covalently linked to the coating.

Adding EDC ("1-Ethyl-3-(3-dimethylaminopropyl)-carbodiimide (EDC) and NHS (N-hydroxylsulfosuccinimide) catalyzes the formation of amide bonds between carboxylic acids or phosphates and amines by activating carboxyl or phosphate to form an O-urea derivative. See Anal. Biochem. 185:131 and Anal. Biochem. 156:220. The coupling may involve the preparation of self-assembled monolayers (SAMs). The substrate, Au on Si, is immersed into an ethanol solution of the desired thiol(s). The tail group that provides the functionality of the SAM can be widely varied. $CH_3$-terminated SAMs are commercially available; other functional groups can be synthesized. In addition, chemical modification of the tail group is entirely possible after formation of the SAM, expanding the available range of functionalities even further. Examples of functionalities used are: —$CH_3$, —OH, —(C=O)O$CH_3$, —O(C=O)$CH_3$, —O(C=O)$CF_3$, —O(C=O)$C_6H_5$, —COOH, and —O$SO_3$H.

Thiols have been functionalized with a variety of headgroups to form SAMs with desired properties. In addition to the above-listed head groups, thiols terminated with nitrilo triacetic acid (NTA) have been shown to self-assemble with ethylene glycol-terminated thiolates to yield a composite surface that specifically binds histidine-tagged proteins while resisting nonspecific adsorption. See, U.S. Pat. No. 5,620,850 to Bamdad, et al., issued 15 Apr. 1997, entitled "Molecular recognition at surfaces derivatized with self-assembled monolayers."

Alternatively, one may form covalent bonds by a process in which gold electrodes are modified with a SAM of cysteic acid N-hydroxysuccinimide. The enzyme is covalently bound to the SAM via amines on side chain lysine groups of the protein, attacking the succinimide and forming an amide. See Willner, M. Lion-Dagan, S. Marx-Tibbon and E. Katz, *J. Am. Chem. Soc.*, 1995, 117, 6581.

Filter

Figure 6:
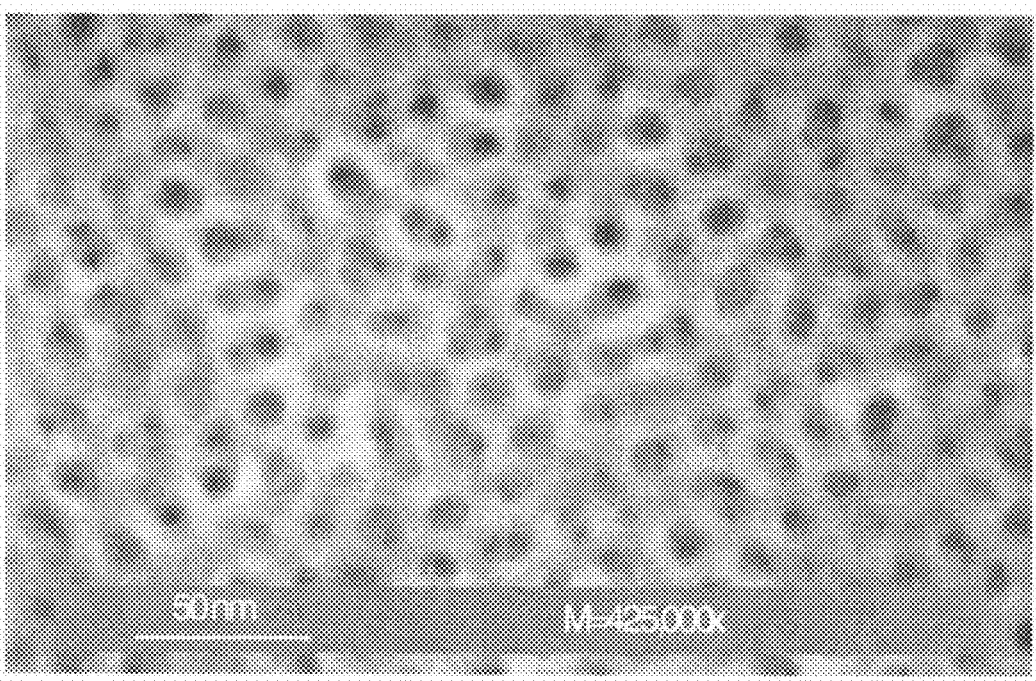
FIG. 6 is an electron micrograph showing a porous $SiO_2$ film with pore sizes between 10-15 nm.

Channel clogging is one of the major issues in nanopore-based devices caused by non-specific adsorption of molecules to the pore. As shown in FIG. 6, a nanoporous silicon oxide film to be employed as filters can be used to further enhance the performance of the present nanopore devices. The present nanopore structures have a gold or noble metal overhang, but are within the pore, rigid membrane material, such as silicon containing compounds, e.g., silicon nitride.

Self-assembling nanoporous thin films of amorphous silicon oxide have been formed by mixing organic amphiphilic template with silicon oxide precursor in ethanol. The template and the silicon oxide precursor co-assemble upon ethanol evaporation and after the thermal removal of the template an ordered silicon oxide porous network is created. The pore diameter can be tuned in the 5-100 nm range. The filter pore size should be tuned to be less than the nanopore diameter.

Moreover, the nanopore wetting issue is minimized in the customized nanopore device since the nanochannels are in ultra-hydrophilic gold thin films. As has been verified in electrical experiments, there were no problems observed in the wetting of the nanopores.

Charge Driven Devices

In order to monitor the nanopore conductivity, a nanopore chip was mounted into a homemade holder separating two fluidic reservoirs called cis and trans, i.e., same side as a sample, and opposite side. After wetting of the nanopore with methanol, the two chambers were rinsed with DI water and filled with pH 6 buffer (1M KCl, 10 mM MES, 10 mM sodium acetate). The ionic current passing through the nanopore was monitored in real-time with a 100 μs sampling period using an Axopatch 200B during the duration of the experiment. The use of a patch clamp amplifier allows one to keep the voltage constant while observing changes in current. Alternately, the cell can be current clamped, keeping current constant while observing changes in membrane voltage.

To measure the effect of current passing through the gold layer on the conductance of the gold-sputtered nanopores, the conductivity of a FIB-drilled nanopore closed by gold-sputtering is obtained. It was found that less than 80 pA flows through the gold when 1V applied across the membrane which may be still due to very small openings.

1. Attachment of Horse Radish Peroxidase

Figure 8:
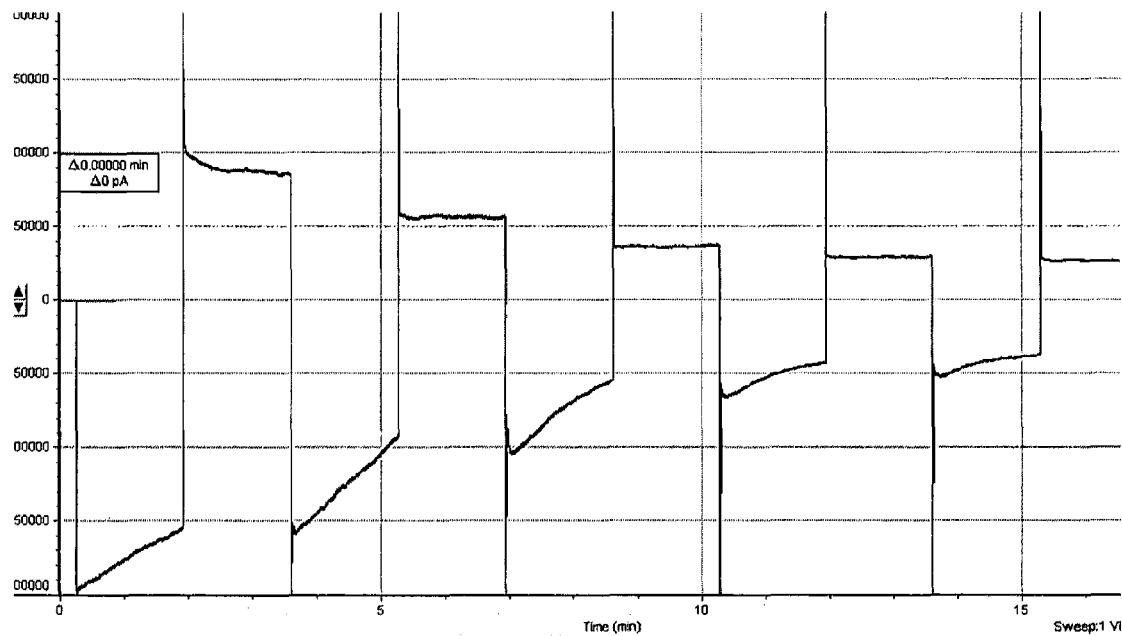
FIG. 8 is a tracing obtained with an Axopatch 200B patch clamp amplifier (Axon Instruments, CA) showing changes in current (pA) from attachment of horse radish peroxidase to a nanopore.

FIG. 8 shows changes in ionic current passing through a nanopore when HRP was attached to a nanopore of 40 nm in diameter by driving the molecules to the pore with applying electrostatic force. FIG. 8 shows a reduction in ionic current from about 200 nA to about 40 nA due to nanopore blockage.

In this example, the attachment of proteins to the nanopore, a chip containing 40 nm×40 nm nanopore is employed. Horseradish Peroxidase (HRP, 40 kDa, pI 8.5) (United States Biochemical) is added to the cis (gold) side of the pore and at a concentration of 0.091 mg/mL. At these conditions HRP is positively charged and the nanopore surface is negatively charged. The binding rate of the protein molecules to the nanopore is not significant; however, by applying electrostatic potential across the nanopore this measure increases. Upon application of the potential with Ag/AgCl electrodes (anode on cis side) across the nanopore, the conductance of the nanopore gradually decreases. This observation can be explained by binding of the proteins in the vicinity of the nanopore driven towards the opening of the pore. In order to exclude the possibility of this effect being due to electrodeposition of HRP to the electrodes, both cis and trans electrodes were switched with fresh ones. It was found that results with different electrodes were consistent. The nanopore conductance finally reaches a steady state value corresponding to attachment of approximately a monolayer of proteins on the surface of the nanopore. However, by removing the applied potential at any point, the nanopore conductance remains constant enabling engineering of the nanopore conductivity.

Figure 9:
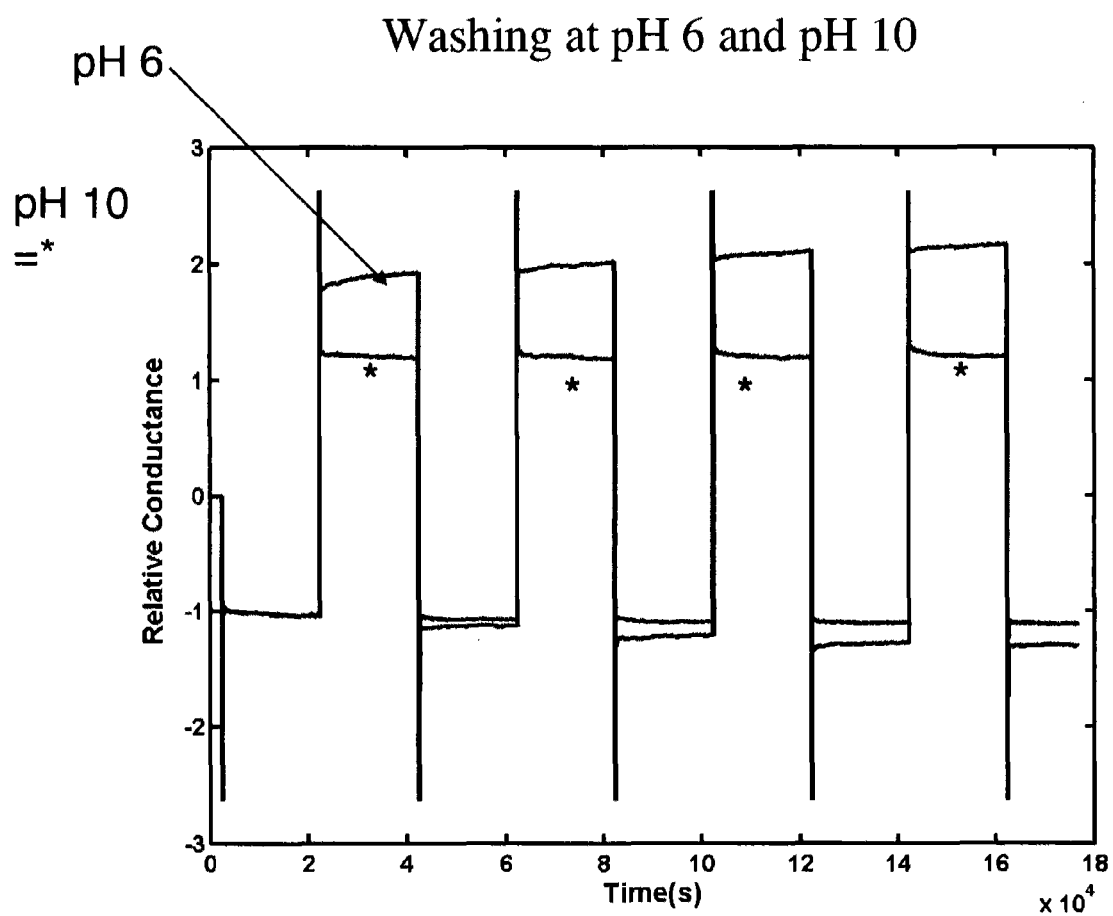
FIG. 9 is a tracing of relative conductance obtained with an Axopatch 200B amplifier after washing with solutions at pH 6 and pH 10.

As shown in FIG. 9, washing with solutions at pH 6 and pH 10 gave different results when measured with an Axopatch 200B instrument. After removing the electric field, the nanopore was washed with buffered solution at pH 6 to wash free proteins away. For studies at pH 6, the cis and trans chambers were filled with 1M KCL, 10 mM MES, 10 mM sodium acetate, pH 6. HRP (pI=8.5) is added to the cis side. By applying positive potential to the cis side relative to the trans chamber, HRP molecules are driven through the nanopore. The ionic current is recorded as HRP molecules bind to the nanopore. The conductance of the pore remained constant during washing; consequently we conclude that the off-rate of the bound proteins at pH 6 is negligible.

This is not the case when the reservoirs are washed with pH 10 solution (1M KCl, 15 mM glycine). At pH 10 the attached proteins are released from the surface and the native form of the nanopore is restored within 89%±6% of the initial conductance. The detachment of HRP molecules at this pH can be explained by considering the electrostatic repulsion of the negatively charged nanopore surface and proteins.

Due to the asymmetric geometry of gold-sputtered nanopores, the rectification of the ionic current through the nanopore can be monitored as a signature of the excess surface charge present on the pore walls. The current rectification factor, |I+(V)/I−(V)|−1, increases considerably after the attachment of proteins to the nanopore wall.

Upon occupation of the binding sites, the conductance of the nanopore is expected to decrease as follows:

$$\frac{dG}{dt} = -G_e k_{on} c(s_{max} - s) = -J_o e^{-\alpha s}(s_{max} - s) \quad (1)$$

where $G_e$ is the unit (due to one protein) conductance change of the nanopore. $J_0$ is a time invariant parameter.

Figure 11:
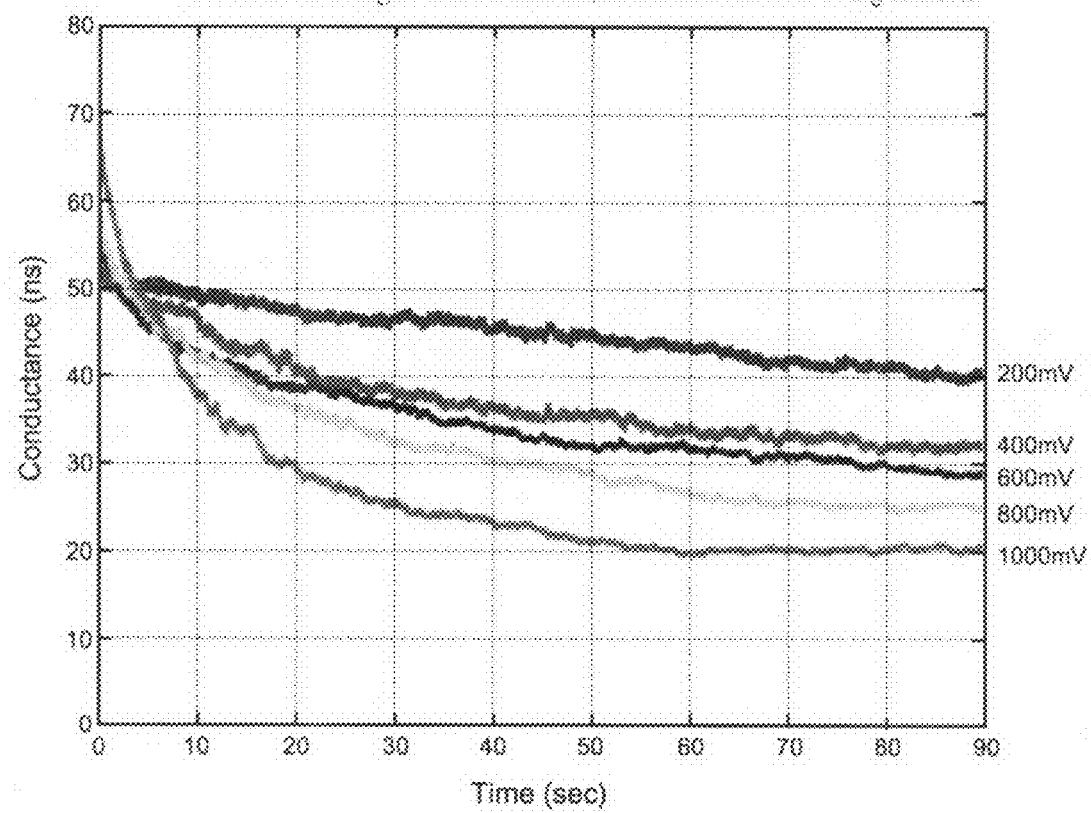
FIG. 11 is a graph showing conductivity change of a nanopore upon binding of HRP (horse radish peroxidase) measured with an Axopatch 200B amplifier for different voltages applied on either side of the nanopore. This graph shows the resistance of a silicon nitride membrane containing an array of nanopores after incubation with different concentrations of antigen. This platform has more than 3 orders of magnitude dynamic range and a sensitivity comparable to ELISA suitable for clinical testing. Presence of hCG with concentrations higher than 3 ng/ml, within the detectable range of the proposed device, is the biomarker of pregnancy.

To explore the validity of the proposed model, experiments were performed to test the voltage dependence of the protein attachment. The clean pore (after pH 10 washing) is flushed with pH 6 solution and HRP is added (0.09 mg/mL). In each sub-experiment 200, 400, 600, 800 and 1000 mV are applied for 90 s respectively and the ionic current passing through the nanopore is recorded (FIG. 11). Equation (1) is fitted to the experimental data (not shown) by optimizing parameters α and $J_o$ to minimize the mean square of error. As it is expected $J_o$ is an exponential function of applied voltage across the nanopore, exp(zeV/kT). The value obtained for z is 0.127±0.009 for all voltages tested.

An assay was performed to establish the activity of HRP after binding upon electrostatic force and it was found that the bound enzyme was still in its active form under the conditions of 1M KCl at pH 6, after 1V had been applied for the duration of a typical experiment.

It follows from these results, that, when one wishes to operate the present device to produce translocation of a molecule through the pore, the applied electric field across the pore should be more than a certain threshold value to get translocation events. Sometimes it is not even possible to force molecules to pass through the nanopore. This obstacle, which is a common and severe problem with synthetic nanopores, is due to the electrostatic interactions between molecules and charged nanopores. Similar behavior is reported where proteins have been shown to have the maximum diffusivity through a nanogap at a pH around their isoelectric point (pI). Since at pI, the net charge of protein is zero and it is not possible to get translocation by electrophoresis. This was observed in the present work where we tried to translocate horseradish peroxidase (HRP with pI of 8.5) through nanopores. At pH 6, in which HRP is positive, we never got translocation and we observed continuous reduction of pores indicating the attachment of HRP molecules to the pore. At pH 10, in which HRP is negative, in some experiments in which applied voltage across the pore is bigger than 0.5V, we observed translocation of proteins. At pH 8, close to the pI of HRP, we were not able to obtain translocation events. A possible solution to manage the molecule-pore interaction in nanopore sensors is the ability to control the nanopore wall potential. Nanopore wall potential was controlled by adding a 3 nm thick $Al_2O_3$ insulating layer to the gold or chromium thin film sputtered on to the thin film to reduce the pore diameter. The nanopore wall potential can be actuated capacitatively using metal film electrodes conformed to the nanopore. Measurements of ionic current passing the nanopore and imaging of concentration polarization of fluorescent dyes in the region near the nanopore. We fabricated synthetic nanopores in freestanding silicon nitride membranes using focused ion milling as described above Gold or chromium thin films were sputtered onto the membrane to reduce the pore diameter and serve as a nanopore wall electrode. The nanopore was then coated with a 3 nm thick $Al_2O_3$ insulating layer by atomic layer deposition. The nanopore wall potential can be actuated capacitively using metal film electrodes conformed to the nanopore and beneath the insulating layer. When a DC voltage is applied to this electrode, a fraction of the wall electrode potential is applied to the electrical double layer, changing the nanopore wall potential.

2. Attachment of Glucose Dehydrogenase

Upon binding of the probe molecule glucose dehydrogenase to the gold-coated nanopore, the ionic current passing through the nanopore reduced due to the partial blockage of the pore.

As shown in FIG. 7A (left), glucose dehydrogenase (GDH) is added for immobilization on the nanopore. GDH has been directed to the pore by utilizing an electric field, essentially as described in the section above. In FIG. 7A (right) GDH is attached to the pore, which causes partial blockage of the nanopore and consequently reduction in ionic current passing through the pore. The electrodes are charged according to the charge on the molecule. In this case, the enzyme is negative, so it will move towards the positive electrode, bottom (7A) and left (7B). GDH is added to the cis (gold) side of the pore. An electrostatic potential of 100 mV is applied across the pore, which drives the protein to the pore. After incubation for 2-3 minutes, the pore was partially blocked due to the GDH immobilization in the nanopore. FIG. 7B illustrates an array of bioactivated nanopores, where an enzyme is bound to an overhang 19 in a metal layer on a silicon membrane 14 having a predetermined number of spaced apart nanopores.

3. Attachment and Detection of Antibody Binding

Figure 10:
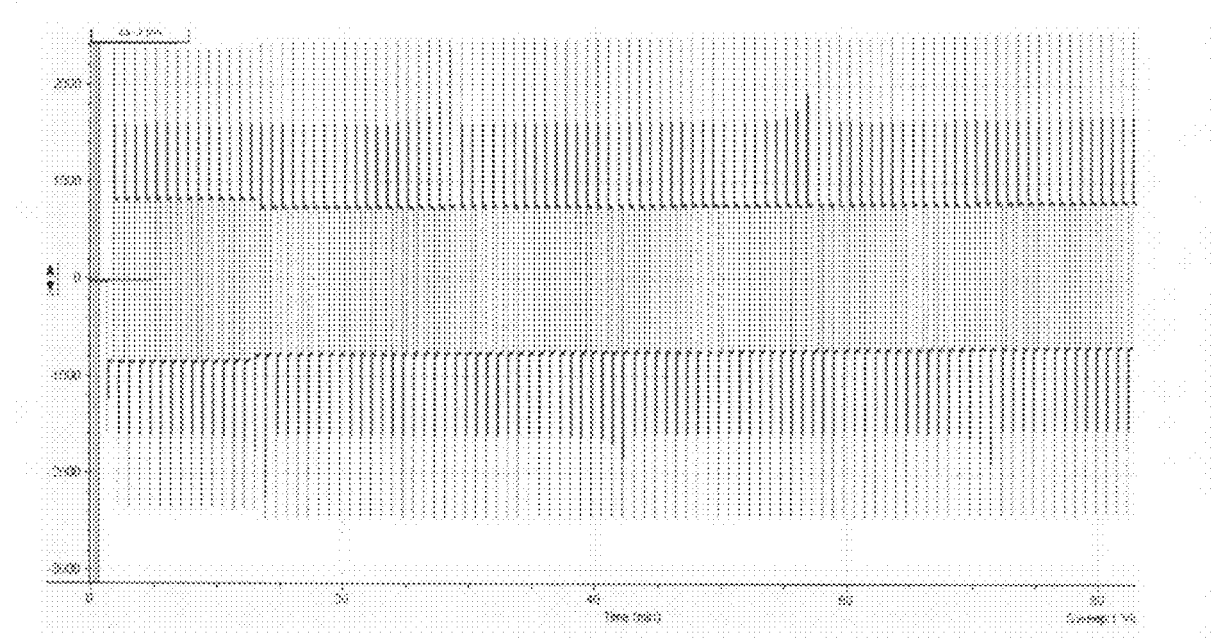
FIG. 10 is a tracing obtained with an Axopatch 200B amplifier showing detection of single antigen-antibody binding.

Antibody to human chorionic gonadatropin (HCG) obtained from Fitzgerald Industries International, Inc. (Concord, Mass.) was attached to a nanopore of 15 nm in diameter by applying 100 mV electrostatic potential across the pore and incubation. The device was placed in a chamber (as shown schematically in FIG. 7) having 100 mM KCl. After attachment of the antibody, the HCG with concentration of 1 µg/ml was added to the cis side. A 200 mV peak-to-peak square wave voltage was applied across the pore. The ionic current was measured with an Axopatch 200B amplifier as shown in FIG. 10. As shown in FIG. 10, after about 15 minutes, the amplitude of the current reduced and stayed constant afterwards for more than an hour. This partial blockage is due to the binding of a single-molecule of HCG to the antibody immobilized in the pore.

In a second protocol, the procedure begins by monitoring immuno-complex formation initially involves recording the ionic current passing though an empty nanopore. Next, the primary antibody is introduced into the nanopore and the current is recorded until an antibody is captured inside or at the entrance of the nanopore. Subsequently, the chambers are washed and the ionic current is re-measured to confirm the bioactivation of the nanopore. Finally, the pre-mixed solution of antigen and secondary antibody is added, and the real-time ionic current recorded to monitor the formation of the immunocomplex. In this example silicon nitride nanopores were fabricated by using FIB as described above. The pore diameter was reduced to 30 nm by gold/chromium sputtering. The chip was clamped in the holder substantially as shown in FIG. 7. As can be seen there, a nanopore array, shown at 19 is provided in membrane 10, which separates into two fluid areas, each with its own electrode. The electrodes are connected to a patch clamp amplifier, which can deliver various waveforms to the electrodes. At times we encountered problems in getting stable ionic currents. This could have resulted from issues in nanopore wetting or contaminations in the pore. Experimentally it is shown that wetting the pores initially with methanol or ethanol and then gradually changing the solution to water with salt can be very helpful. In addition, sometimes leaving the pore under bias for long time can stabilize the conductance of the pore. After the chip was successfully wetted, the nanopore received a slow injection of a pH 6 buffer (100 mM KCl, 10 mM MES, and 10 mM sodium acetate). A square wave voltage was applied across the chip with 400 mV peak-to-peak amplitude. Recordings were made with a sampling rate of 5 kHz. This rate is sufficiently fast to capture interaction information. The ionic current was amplified with Axopatch 200B (Molecular Devices, CA), digitized with Digidata 1322A (Molecular Devices, CA) and recorded with pClamp9 software (Molecular Devices, CA). Before injecting the primary antibody solution, the current level passing through the nanopore is measured. The peak-to-peak steady-state current was 600pA with rectification of about 5%. With this background information logged, the primary antibody solution was added to the nanopore device. HCG monoclonal antibody (Fitzgerald, MA) with a concentration of 0.5 mg/ml (equivalent to >>5 nM) in the same buffer solution used above was added. Ionic current passing through the pore was monitored in real-time by applying the same square wave across the pore and recorded for further analysis. Electrical measurements of the nanopore yield real-time data reflecting the status of the pore. This method allows for bioactivation of the pore to be detected in real-time, and for excess molecules to be washed off instantly.

After about 40 minutes, the fist partial blockage event was detected. We interpreted this event as an antibody binding near the pore. Seven minutes after the initial binding, the secondary binding event occurred. Based on the change in current from the first binding event, the blockage of this proceeding event was three times greater than the initial blockage as a result of antibody immobilization in the nanopore. Empirically, what can be seen is a drop from the background peak-to-peak current of 600 pA to post antibody capture current of 460 pA. In relative terms, a 23% blockage is seen as deviated from the background and the ionic current rectification was increased to 10%, as a result of the change in surface charge profile of the pore. The chip was then washed with washing buffer solution to remove unbound and excess antibodies. After washing, the ionic current remained the same confirming that the antibody had in fact been immobilized. The first partial binding event was detected about 40 minutes after injection of the primary antibody to the nanopore. The immobilization of the antibody on the nanopore happened after 7 minutes. The same time lag was observed in other experiments with immobilization of enzymes to the nanopore. We believe the reason for the faster binding in the second event relative to the primary binding is due to the cooperative interaction of the immobilized proteins, i.e., protein-protein interactions on the surface. Protein-protein interaction increases the affinity of the protein to the surface, which in turn increases the immobilization rate of the antibody molecules. After the nanopore bioactivation is accomplished, we continue electrical measurements of the pore to monitor the status of the antibody attached to the pore. First, the secondary antibody with concentration of 4 µg/ml (~20 nM) is added as a control experiment. During 30 minutes of incubation, no further sudden blockage in ionic current was detected. Finally, the pre-mixed solution of antigen and secondary antibody, with concentrations of 0.2 µg/ml (~5 nM) and 4 µg/ml (~20 nM) respectively, was added. Incubation of the secondary antibody with a lower molar concentration of antigen provides an environment where the majority of the antigens in the mixture are bound to the secondary antibody. The ionic current is acquired again using the 400 mV peak-to-peak square wave pulses. Within 30 s of injection, current reduces by about 50%, indicating another binding event.

Quantification of Protein Biomarkers

Figure 12:
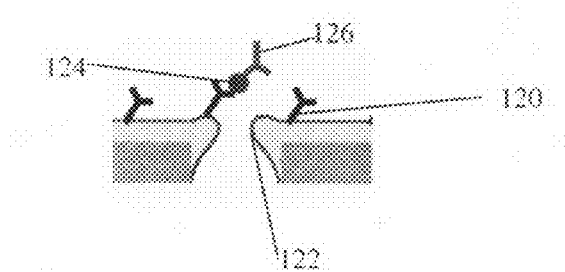
FIG. 12 a schematic showing an antibody capture scheme.
Figure 13:
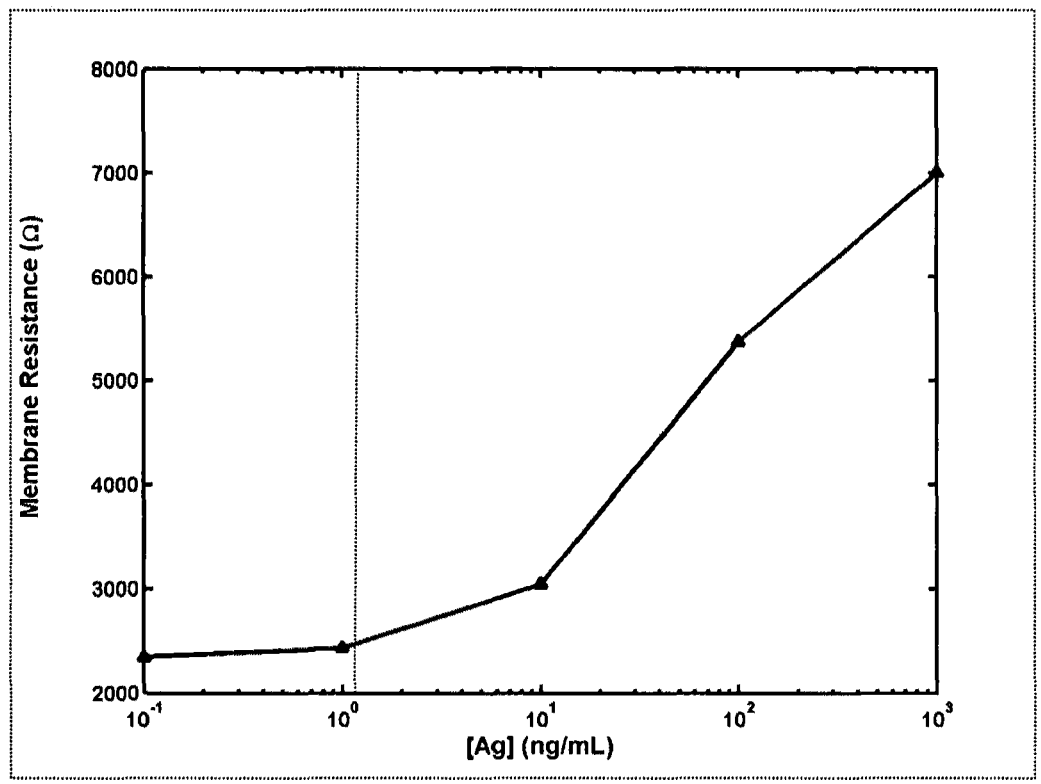
FIG. 13 is a graph showing results in a format useful for a pregnancy test, based on HCG binding to an antibody on a nanopore.

Using an array of bioactivated nanopores, we have demonstrated the quantification of hCG concentration with high sensitivity and dynamic range. FIG. 12b illustrates a primary antibody immobilized with its Fc portion 120 on a substrate near nanopore 122 having an overhang. The antigen (HCG) 124 preincubated with secondary antibody 126 then binds to the primary antibody if it was present in the sample and complexed to the secondary antibody in a incubation previous step. The same platform can be used for analyzing other protein biomarkers. The fabrication of arrays of nanopores is similar to the single pores. In the milling step, we drill arrays of pores instead of single nanopores. The nanopores are provided with overhangs and antibody is attached to a SAM by incubating the antibody solution (with a concentration of 5 nM) with the chip overnight. After washing the unbound antibodies off, the chip is clamped in the chip holder. First, we measure the current passing through the pores to record the initial conductance. Then, we incubate the chip with the most dilute antigen solution. All of the antigen solutions are pre-incubated with secondary antibody solution (with a concentration of 20 nM). After 15 minutes of incubation, we increase the concentration of antigen solution and we continue this cycle to arrive at the readings for different antigen concentrations. Like ELISA, the number of antigen molecules bound to the surface is proportional to the antigen concentration. As a result, for more concentrated antigen solutions, more nanopores are blocked partially with bound immunocomplexes. The experimental data for the conductance change upon increasing the concentration of hCG is demonstrated in FIG. 13. The membrane resistance (related to amount of antigen present) on the left side of the dotted line is equivalent to ELISA sensitivity. The area to the right of the dotted line is the amount of antigen present in a positive pregnancy test.

Direct Detection of DNA Hybridization

Figure 14:
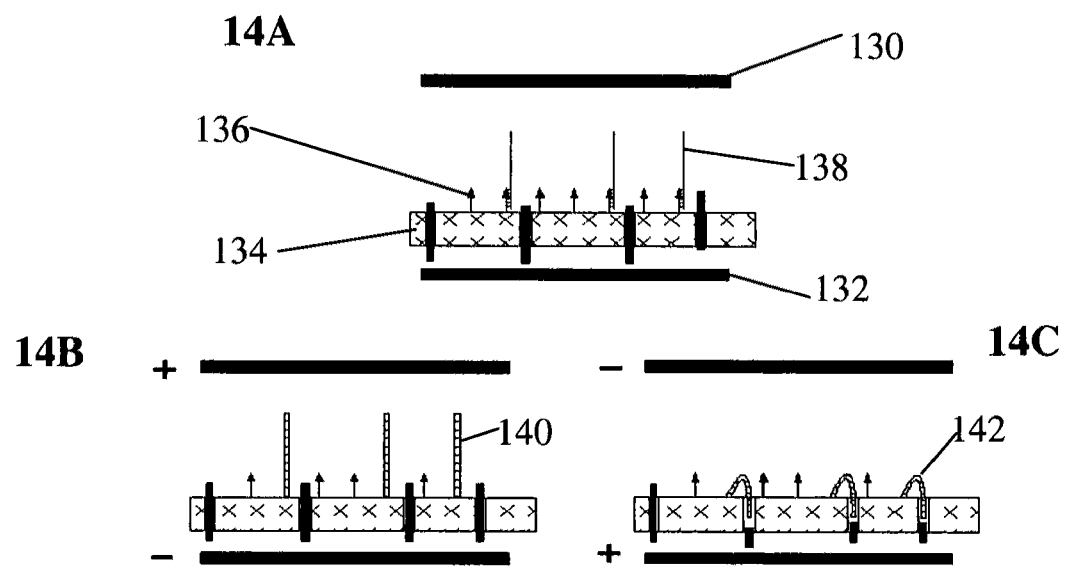
FIG. 14A-C is a diagrammatic view of an embodiment of the present device in which polynucleotide strands are immobilized on s substrate, near nanopores (A); a current is applied to extend the strands (B); and the strands change conformation to obstruct nanopores (C).

In this embodiment, polynucleotide (e.g., DNA) strands are immobilized near the nanopores, as shown in FIG. 14. Electrodes 130 and 132 above and below, respectively, a nanopore chip 134 are initially uncharged, as shown in FIG. 14A. Probe strands 136 are immobilized on the surface, and some will be near the nanopores having overhangs. Three nanopores are illustrated. If hybridization occurs with target polynucleotide strands 138 a duplex is formed, and a longer molecule results. As shown in FIG. 14B, the now longer strands stand up from the surface in response to a positive charge on electrode 130 attracting the negatively charged biopolymer. If electrode polarity is reversed, the polynucleotide hybrid now curves down and towards the nanopore in the surface to which it is immobilized, as shown at 142, causing nanopore blockage.

Using an array of bioactivated nanopores, the hybridization of single-stranded DNA (ssDNA) molecules to complementary immobilized oligonucleotide probes was electrically detected. We have demonstrated the ability to bioactivate the pores with short-length oligos (20-base), and further, detect hybridization with the target DNA (303-bases). The oligonucleotides LS-Biotin-F (5'-GGATCATGTAACTCGCCT-TGA) (SEQ ID NO: 1) and LS-R (5'-GGGAGGGCTTAC-CATCTGG) (SEQ ID NO: 2) were synthesized as the primers for partial amplification of pUC19 (Biolabs, MA, USA). The oligonucleotide probe, LS-F-thiol-(5'-GGGATCATG-TAACTCGCCTTGA) (SEQ ID NO: 3), was synthesized for immobilization on the nanopores. A 135-base long oligonucleotide (BG-pUC-upper-135b), complementary to the probe, was also synthesized as control ssDNA for hybridization reactions; BG-pUC-upper-135b-(5'-GAGTA AGTAG TTCGC CAGTT AATAG TTTGC GCAAC GTTGT TGCCA TTGCT ACAGG CATCG TGGTG TCACG CTCGT CGTTT GGTAT GGCTT CATTC AGCTC CGGTT CCCAA CGATC AAGGC GAGTT ACATG ATCCC). (SEQ ID NO: 4) All the oligonucleotides were synthesized and HPLC purified by Operon Biotechnologies Inc (AL, USA).

PCR Amplification of Double-Stranded DNA

Amplification was performed on the pUC19 vector by using LS-Biotin-F and LS-R primers for partial amplification of a 303-base pair fragment. Polymerase chain reaction (PCR) was carried out in total volume of 50 μl containing 25 μl HotStar Taq Master Mix (Qiagen, Hilden, Germany), 10 pmole of each primer and water. The PCR reaction was initiated with a 15-minute heated lid denaturation step at 95° C., followed by 35 cycles of amplification with GenAmp 9700 thermocycler (Applied Biosystems, Foster city, CA). Each cycle comprised of a denaturation step at 94° C. for 50 sec, a primer-annealing step at 55° C. for 59 sec, and a chain elongation step at 72° C. for 1 min. The final elongation step was prolonged by 10 min to ensure a complete extension of the amplified DNA.

Solid-Phase Preparation of Single-Stranded DNA

To make ssDNA molecules, a mixture of 50 μl of biotinylated PCR product and 50 μl of Binding Buffer (10 mM Tris-HCl, 2 M NaCl, 1 mM EDTA and 0.1% Tween 20) was immobilized onto M-280-streptavidin super paramagnetic beads (Invitrogen, Carlsbad, USA) by incubation at 43° C. for 30 minutes. The immobilized PCR product was incubated in 20 μl 0.2 M NaOH for 5 minutes. The free, nonbiotin-labeled ssDNA was separated with an MPC magnet (Invitrogen) and was immediately neutralized and purified using MiniElute kit (Qiagen) according to the manufacturer's instructions. The concentration of ssDNA was measured by Agilent 6000 Pico RNA chip using Agilent 2100 bioanalyzer platform (Santa Clara, USA).

The ssDNA was also sequenced by Pyrosequencing technology to monitor the quality of the ssDNA. In brief, 0.4 pmole ssDNA was annealed to 0.4 pmole LS-Biotin-primer at 90° C. for 3 minutes in a total 10 μl annealing buffer (20 mM Tris-Acetateand 5 mM magnesium acetate). The ssDNA and primer hybrid was then mixed with Pyrogold reaction enzyme and substrate and was sequenced by PSQ Pysequencer (Biotage, Sweden) according to the manufacturer's instructions.

DNA Hybridization Detection

Figure 15:
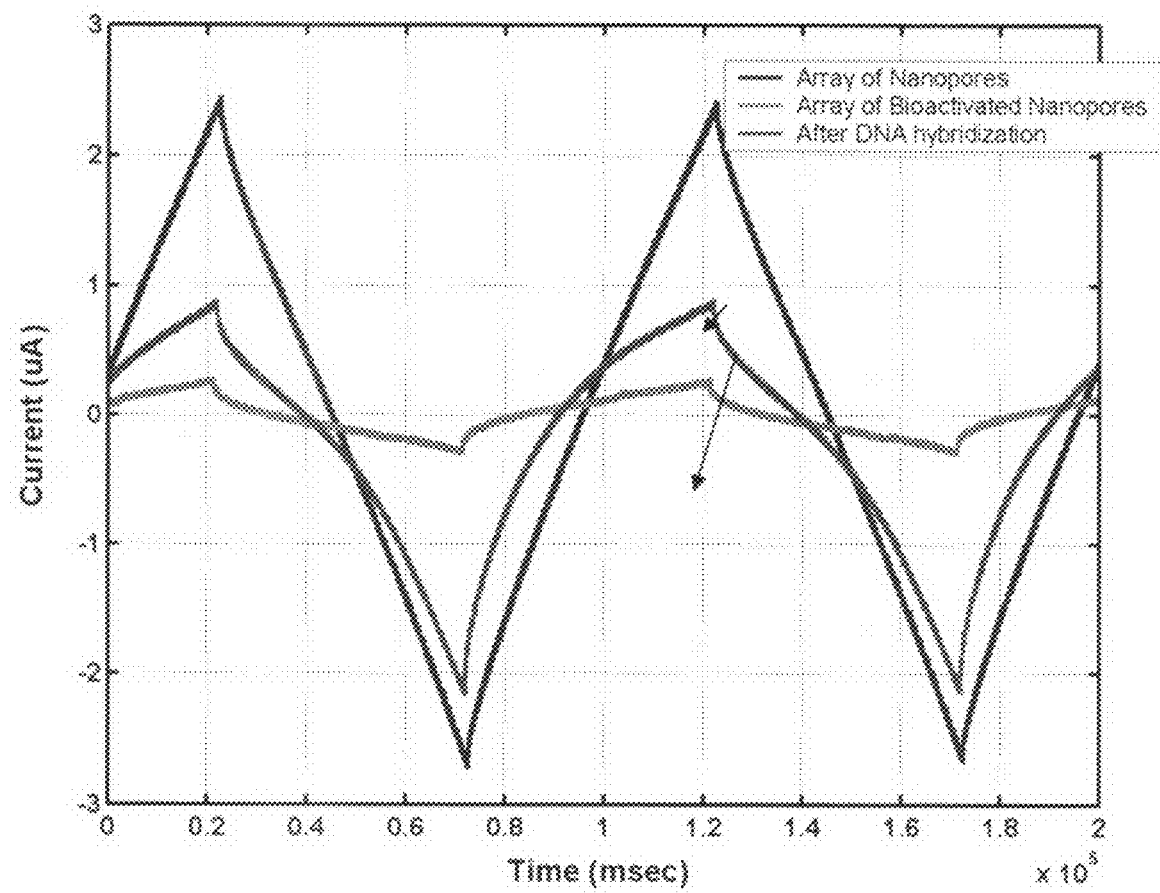
FIG. 15 is a graph current change after DNA hybridization to a DNA strand immobilized adjacent to a nanopore.

After the nanopore device was successfully wetted, the ionic current passing through the array of nanopores was measured in a pH 6 buffer (100 mM KCl, 10 mM MES, and 10 mM sodium acetate) by applying a triangular-wave voltage with 200 mV peak-to-peak amplitude. With this background data logged, the device was incubated with 1 μM LS-F-thiol oligos overnight. The thiolated oligos bound to the gold-coated nanopores. The device was then washed with the same buffer and the ionic current passing through the pores was measured. As shown in FIG. 15, the current rectification remained the same, but the current level reduced. The bioactivated nanopores were then incubated with 303-base long target ssDNA molecules with concentration of 65 nM for 2 hours. Thereafter, the ionic current passing through nanopores was monitored in the same buffered solution. Interestingly, the nanopores were rectifying and the current level increased and became more linear as shown in FIG. 15. Based on other control experiments, we found that the rectification change of the pores is directly related to the ssDNA hybridization to the pores; however, the current level changes were not reproducible. This experimental finding is in agreement with the previous reports on the variation of nanopore conductances within different days. However, the current signature between hybridized and non-hybridized DNA was consistently measurable.

Continuum Modeling of the Protein/Nanopore Structure with the External Electric Field Applied Across Nanopores.

Such an approach offers a useful solution for efficient bioengineering system simulation with relatively modest computational requirements. The continuum-based approach is valid to model the ionic current conduction in the protein/nanopore system under study. The pore size is in the tens of nanometer range; therefore, the finite ion and water molecule sizes can be neglected. Due to the applied external bias, the entire system is under non-equilibrium condition. The electrostatic potential and the distribution of the ion concentration at each lattice point are calculated by solving the set of Poisson-Nernst-Planck (PNP) equations:

$$\nabla \cdot \in \nabla \phi + (C^+ - C^- + \delta \rho) = 0$$

$$\delta C^+/\delta t - \nabla \cdot [D^+ \nabla C^+ + \mu^+ C^+ \nabla \phi] = 0$$

$$\delta C^-/\delta t - \nabla \cdot [D^- \nabla C^- - \mu^- C^- \nabla \phi] = 0$$

where $\phi(r)$ is the electrostatic potential, $\in(r)$ the dielectric constant, $\delta p$ the fixed charge density, $D+/-$ the ion diffusion coefficients, $\mu+/-$ the ion mobilities, and $C+$ and $C-$ cation and anion densities, respectively. The PNP equations are numerically solved using PROPHET, a know partial differential equation solver. This technique is further described in Talasaz et al., "Prediction of protein orientation upon immobilization on biological and nonbiological surfaces," *Proc Natl Acad Sci USA*, 2006 October 3; 103(40): 14773-14778. The probe molecule we used is myokinase, an enzyme with huge hinge bending. The mean distribution of the cations and anion are numerically calculated by PROPHET for different voltages applied across the nanopore. Consequently, the conductivity of the nanopore is estimated. For low voltages, the I-V curve is nonlinear; which is logical due to the nonlinear behavior of the EDL at the protein/solution interface. For larger voltage, the I-V curve is almost linear since the effect of the protein partial charges are negligible. The current blockage due to bioactivation of the nanopore is about 40%, which has been confirmed with experimental observation.

It is worth it to mention that in the above simulation, the surface of the nanopore. In practice, the zeta potential and consequently the surface charge of the nanopore might be nonzero. However, the surface charge of the nanopore can be easily considered.

Alternative Embodiments and Applications

The present device is useful to detect small amounts of analyte (down to a single molecule) found in a sample. The analyte need not be labeled in any way. It is simply driven to or through the functionalized nanopore, where it reacts with the selected biomolecule. The sample fluid is driven through the nanopore mechanically, or, if the analyte is charged, it may be driven though the pore by ionic forces. The device may be used to detect the single antigen/antibody interaction. In this embodiment, one attaches one antibody as the probe molecule to the nanopore: The immobilization is confirmed by monitoring the ionic current passing through the pore. Then, one adds the corresponding antigen: The binding of antigen to antibody will be analyzed by monitoring the ionic current.

The present device may also be used to detect the conformational change of the enzymes during catalytic activity. One attaches the enzyme as the probe molecule to the nanopore, then adds the corresponding substrate. The conformational change of the enzyme will cause a change in the effective opening of the nanopore, resulting in a change in ionic current through the nanopore, which can be measured using existing instrumentation. The pulse rate of the current change will depend on the turnover rate of the enzyme-substrate reaction.

Numerous enzymes are known to undergo significant conformational change during substrate or cofactor binding. A list of specific enzymes may be found in Gutteridge et al., "Conformational changes observed in enzyme crystal structures upon substrate binding," *J. Mol. Biol.*, 2005, 346 21-28, and references cited therein. Of particular interest herein are enzymes undergoing domain motion upon substrate binding.

Of particular interest are diagnostic enzymes such as 3-α-Hydroxysteroid Dehydrogenase (3-α-HSD); Uricase; S-Adenosyl-L-homocysteine Hydrolase; β-N-Acetyl-D-glucosaminidase; Creatinine Deiminase; Fructosyl Amine-Oxygen Oxidoreductase (FAOD); Adenosine Deaminase; Xanthine Oxidase; Glucose-6-phosphate Dehydrogenase; Ascorbate Oxidase; Peroxidase; Creatinine Amidohydrolase; Creatine Amidinohydrolase; Sarcosine Oxidase; Phosphoenolpyruvate Carboxylase; Purine Nucleoside Phosphorylase; 5'-Nucleotidase; and other DNA polymerases and nucleases.

The present device can also measure the substrate concentration. The ionic current will be modulated during catalytic activity of the enzyme. Since the reaction rate and the substrate concentration are related, the substrate concentration will be quantified by measuring the frequency of the conformational change of the enzyme. The use of an array of nanopores means that, with a defined number of nanopores in the membrane, the rate at which the current though the nanopores in the membrane is reduced is a function of the rate of blockage of the nanopores, which, given a fixed reaction rate constant, will be proportional to concentration of the analyte.

Also contemplated herein are devices with a plurality of membranes in a single chamber. In this embodiment, analytes will pass through at least one membrane and contact a second membrane. Different probe molecules may be used to carry out a step-wise analysis. For example, a protease may first be used to cleave a protein to be analysed, and the activity of an active fragment measured in a second membrane.

CONCLUSION

The above specific description is meant to exemplify and illustrate the invention and should not be seen as limiting the scope of the invention, which is defined by the literal and equivalent scope of the appended claims. Any patents or publications mentioned in this specification are indicative of levels of those skilled in the art to which the patent pertains and are intended to convey details of the invention which may not be explicitly set out but which would be understood by workers in the field. Such patents or publications are hereby incorporated by reference to the same extent as if each was specifically and individually incorporated by reference, as needed for the purpose of describing and enabling the method or material referred to.

What is claimed is:

1. A nanopore structure for use in a biosensor, comprising:
   (a) a membrane which is less than about 200 nm thick;
   (b) a nanopore aperture through said membrane, having a diameter through said membrane of less than about 1 µm;
   (c) an annular overhang, comprising a gold surface shaped axially outwardly from the membrane, at an end of the aperture, the overhang shaped axially outwardly from the membrane and radially inwardly to narrow the walls of the nanopore aperture along a fixed axial distance, producing a reduced diameter and a reduced length relative to the original aperture, wherein said reduced diameter is between about 1 nm and about 100 nm, said reduced length is between about 5 and about 100 nm; and
   (d) a biopolymer probe molecule attached to the gold surface on the annular overhang.

2. The nanopore structure of claim 1, comprised in a plurality of nanopore structures, each having an overhang, wherein each overhang has a biopolymer probe molecule covalently attached thereto.

3. The nanopore structure of claim 2 wherein covalent attachment is through an alkyl thiol group.

4. The nanopore structure of claim 1 wherein the membrane comprises silicon nitride or silicon oxide.

5. The nanopore structure of claim 4 wherein the membrane is between about 20 and about 100 nm thick.

6. The nanopore structure of claim 1 wherein the layer forming the overhang is between about 5 and about 70 nm thick.

7. The nanopore structure of claim 1 wherein the membrane is on a support, and the support comprises an aperture communicating with the nanopore.

8. The nanopore structure of claim 7 wherein the support comprises silicon.

9. A nanopore structure according to claim 1 wherein the nanopore diameter is between about 20 nm and about 1 µm.

10. The nanopore structure of claim 1 where the membrane is between about 20 and about 200 nm thick.

11. A nanopore device comprising a nanopore structure according to claim 1, further comprising:
    (a) a first chamber for holding a sample fluid on a first side of the nanopore structure, having said overhang;
    (b) a second chamber on a second side of the nanopore structure in fluid communication with the first chamber through the nanopore aperture;
    (c) electrodes in said first chamber and second chamber for creating ionic current through the nanopore aperture;
    (d) instrumentation for detecting changes in ionic current due to molecules in said sample fluid binding to said probe molecule.

12. The device of claim 11 comprising a membrane having thereon a plurality of said nanopore structures.

13. The device of claim 11 wherein probe molecule is attached through an alkyl thiol group.

14. The device of claim 11 wherein the membrane comprises silicon nitride or silicon oxide.

15. The device of claim 11 wherein the membrane is between about 50 and about 100 nm thick.

16. The device of claim 11 wherein the layer forming the overhang is between about 5 and about 20 nm thick.

17. The device of claim 11 wherein the support comprises silicon.

18. The device of claim 11 where said instrumentation comprises an amplifier for delivering a current through the nanopore aperture.

19. The device of claim 18 where the instrumentation comprises a patch clamp amplifier.

20. The device of claim 11 wherein the probe molecule is a biopolymer selected from the group consisting of antibodies, enzymes and polynucleotides.

21. The nanopore structure of claim 1, wherein the biopolymer probe molecule is selected from the group consisting of antibodies, enzymes and polynucleotides.

22. The nanopore structure of claim 21, wherein said nanopore has an aspect ratio of less than about 5.

\* \* \* \* \*